US00PP33920P3

(12) United States Plant Patent
Los et al.

(10) Patent No.: US PP33,920 P3
(45) Date of Patent: Feb. 1, 2022

(54) ***MANDEVILLA* PLANT NAMED 'PATMANROS3'**

(50) Latin Name: ***Mandevilla sanderi* (Hemsl.) Woodson**
Varietal Denomination: PATMANROS3

(71) Applicant: Patio Plants V.O.F., Klazienaveen (NL)

(72) Inventors: Martijn Los, Klazienaveen (NL); Maurits van den Arend, Klazienaveen (NL)

(73) Assignee: Patio Plants V.O.F., Klazienaveen (NL)

( * ) Notice: Subject to any disclaimer, the term of this patent is extended or adjusted under 35 U.S.C. 154(b) by 0 days.

(21) Appl. No.: 17/239,230

(22) Filed: Apr. 23, 2021

(65) Prior Publication Data

US 2021/0337712 P1 Oct. 28, 2021

(30) Foreign Application Priority Data

Apr. 23, 2020 (QZ) ..... PBR 2020/1114

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 6/088; A01H 5/02
See application file for complete search history.

*Primary Examiner* — Keith O. Robinson
(74) *Attorney, Agent, or Firm* — Samuel R. McCoy, Jr.

(57) ABSTRACT

A new and distinct *Mandevilla* plant named 'PATMANROS3' which is characterized by an upright and freely branching growth habit, an abundance of dark green foliage, flowers with a white outer floral tube, very light red-purple flower petals that become progressively darker towards and at the margins, a dark red-purple to orange-red inner floral tube, as well as the stability of these characteristics from generation to generation.

3 Drawing Sheets

Latin name of the genus and species: The Latin name of the genus and species of the novel variety disclosed herein is *Mandevilla sanderi* (Hemsl.) Woodson.

Variety denomination: The inventive variety of *Mandevilla* disclosed herein has been given the variety denomination 'PATMANROS3'.

CROSS REFERENCE TO RELATED APPLICATIONS

This application claims priority to the Community Plant Variety Rights application number 2020/1114, filed Apr. 23, 2020, which is herein incorporated by reference.

BACKGROUND OF THE INVENTION

Parentage: The new plant originated as a seedling selection from the open pollination of a plurality of cultivated *Mandevilla sanderi* 'Velvet' plants (not patented), the seed parent, and unnamed *Mandevilla sanderi* plants (not patented) in the spring of 2017. The true pollen parent is unknown. Seed was collected from the 'Velvet' plants and germinated at a greenhouse in Klazienaveen, The Netherlands. The resulting seedlings were grown to maturity and observed for unique characteristics. In March of 2018, the claimed plant was observed to exhibit a unique flower color relative to the other seedlings from said cross of 2017 and was selected for commercialization.

Asexual Reproduction: Asexual reproduction of the new cultivar 'PATMANROS3', by way of softwood stem cuttings, was first initiated in March of 2018 in Klazienaveen, The Netherlands. Through more than 6 subsequent generations, the unique features of this cultivar have proven to be stable and true to type.

SUMMARY OF THE INVENTION

The cultivar 'PATMANROS3' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'PATMANROS3'. These characteristics in combination distinguish 'PATMANROS3' as a new and distinct *Mandevilla* cultivar:

1. *Mandevilla* 'PATMANROS3' exhibits an upright, freely branching growth habit; and
2. *Mandevilla* 'PATMANROS3' 'PATMANROS2' exhibits an abundance of dark green foliage; and
3. *Mandevilla* 'PATMANROS3' exhibits large flowers; and
4. *Mandevilla* 'PATMANROS3' exhibits flowers with a white outer corolla tube; and
5. *Mandevilla* 'PATMANROS3' exhibits flower petals that are very light red-purple, generally appearing as very pale pink, which become progressively darker red-purple towards and at the margins when fully opened; and
6. *Mandevilla* 'PATMANROS3' exhibits with a dark red-purple to orange-red inner corolla tube.

BOTANICAL DESCRIPTION OF THE PLANT

Figure 1:
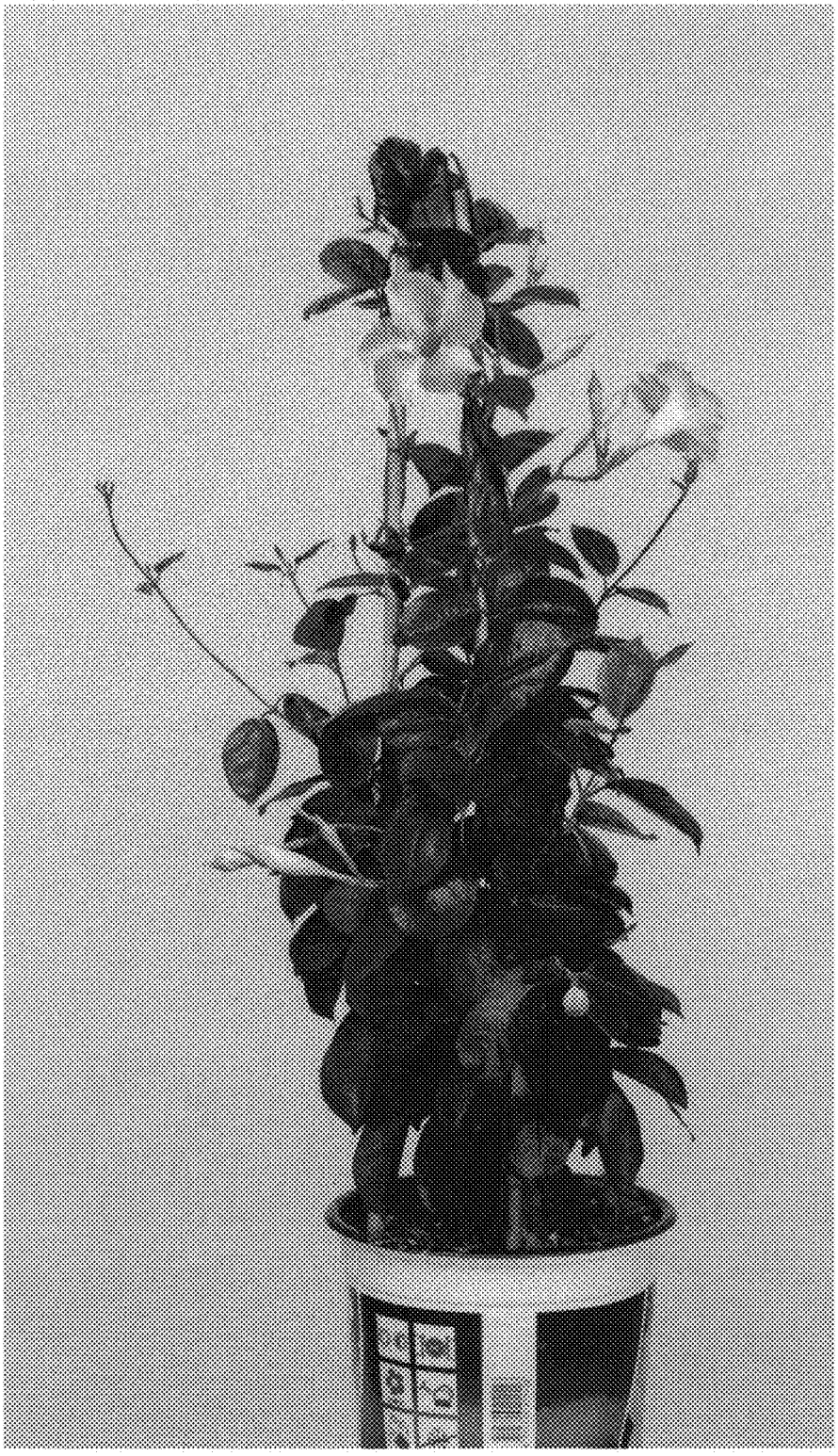
FIG. 1 illustrates, as nearly true as it is reasonably possible to make the same in color photographs of this type, an exemplary 12 month old 'PATMANROS3' plant in a 17 cm nursery pot, grown in a greenhouse in Klazienaveen, The Netherlands.
Figure 2:
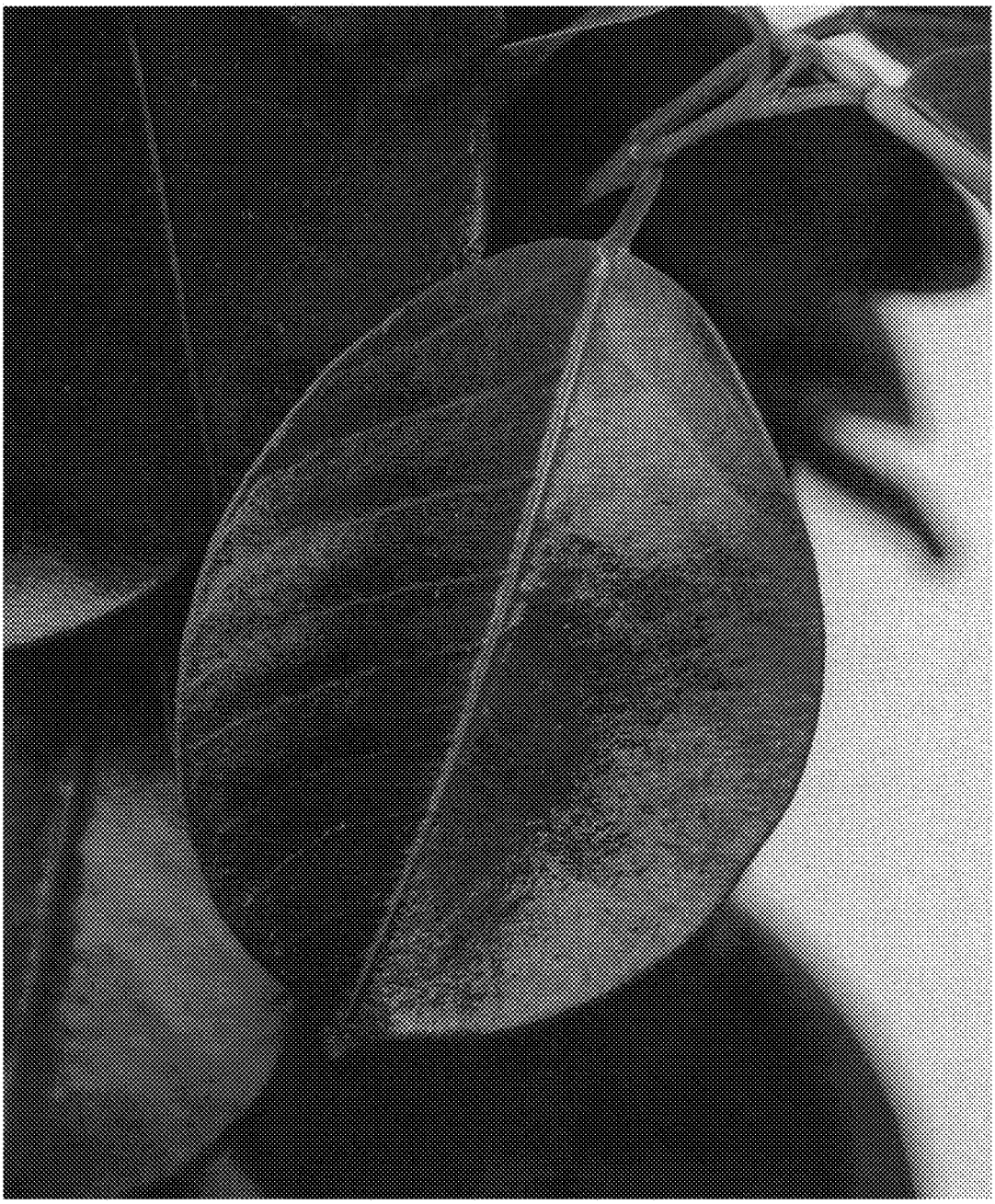
FIG. 2 illustrates, as nearly true as it is reasonably possible to make the same in color photographs of this type, the mature foliage of 'PATMANROS3'.
Figure 3:
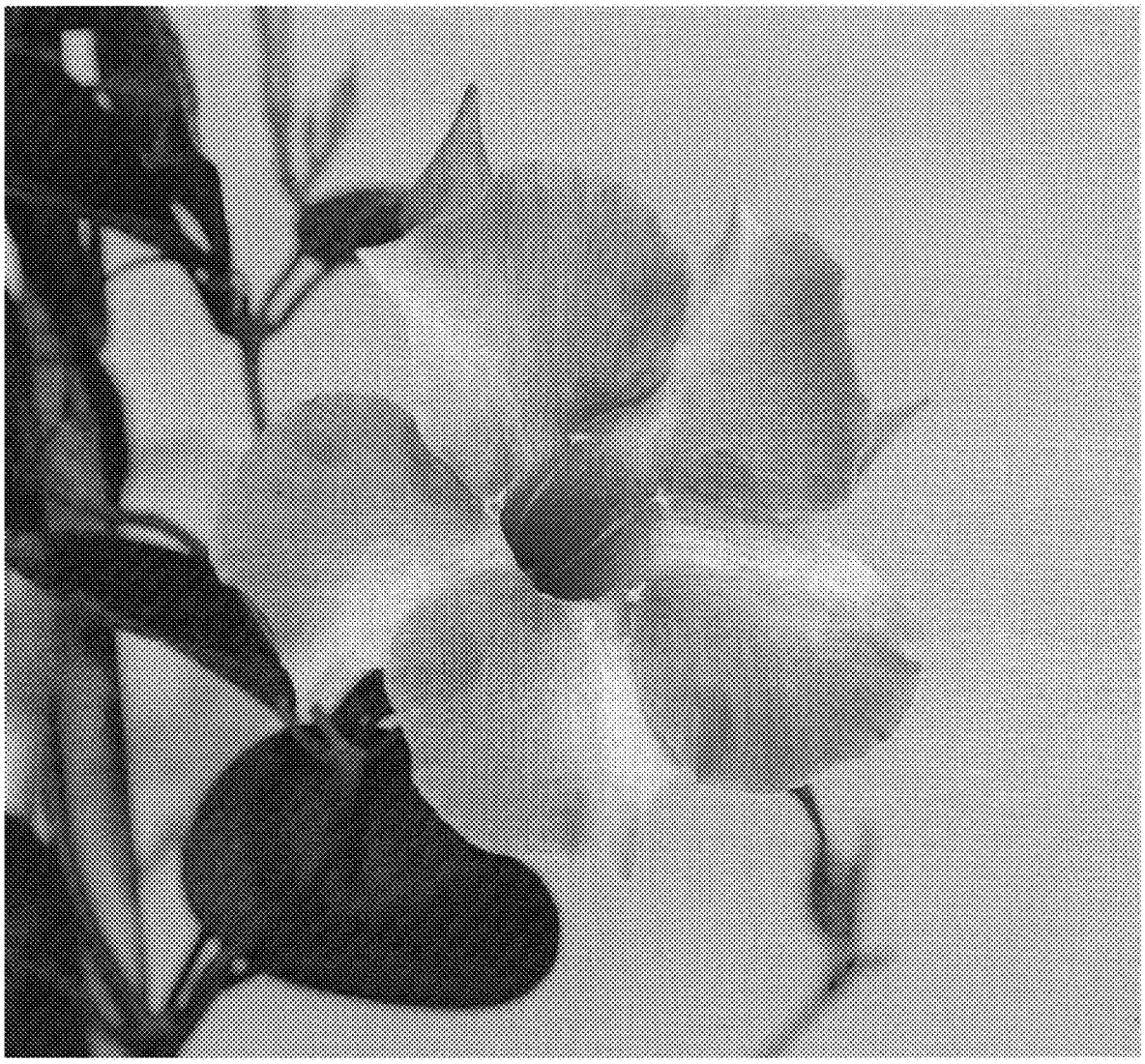
FIG. 3 illustrates, as nearly true as it is reasonably possible to make the same in color photographs of this type, an exemplary flower of 'PATMANROS3'.

The following observations and measurements were made in April of 2021 and describe averages from a sample set of six specimens of 12 month-old 'PATMANROS3' plants grown in 17 cm nursery pots grown in a greenhouse in Klazienaveen, The Netherlands. Plants were produced using conventional greenhouse production protocols for *Mandevilla* which consisted of regular overhead and ebb and flood irrigation and fertigation applications. Pest or disease control measures were utilized in production as required. Plants were produced with full sun exposure and no photoperiodic treatments or artificial light was given to the plants.

Those skilled in the art will appreciate that certain characteristics will vary with older or, conversely, with younger plants. 'PATMANROS3' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'PATMANROS3' and comparisons with the parents and most similar commercial variety of *Mandevilla* are provided below.

Plant description:

*Growth habit.*—Vining perennial; broad upright.

*Plant shape.*—Ovate to obovate to broad obovate.

*Average height from base to top of foliage.*—58.8 cm.

*Average height from base to top of the floral plane.*—54.0 cm.

*Average width.*—36.2 cm.

*Growth rate.*—Moderately fast.

*Plant vigor.*—Moderately vigorous.

*Propagation method.*—Softwood stem cuttings; rooting is in initiated in approximately 21 days, with a fully rooted cutting in approximately 6 weeks, when grown in a greenhouse with an ambient average temperature of 28 to 30 degrees Celsius.

*Time to produce a finished plant.*—Approximately 9 to 12 months is required to produce a fully rooted and marketable 19 cm plant when grown under greenhouse conditions.

*Disease and pest resistance or susceptibility.*—Plants have not been observed to be susceptible or resistant to pathogens and pests common to *Mandevilla sanderi*.

*Environmental tolerances.*—Adapt to at least USDA Zones 10 and 12, and temperatures ranging from at least 5 degrees to 40 degrees Celsius; moderate tolerance to rain; low to moderate tolerance to wind; low tolerance to drought.

Root system:

*General.*—Freely branching; moderately dense rooting.

*Texture.*—Fibrous.

*Color.*—Greyed-orange, nearest to a mixture of RHS 165C and 166D.

Stem:

*Branching habit.*—Basally branching main stem; freely branching with vining lateral branches which are void of tendrils or anchoring roots. Stems and branches exude a milky exudate when damaged.

*Number of main stems per plant.*—8.

*Number of lateral branches per plant.*—16.

*Aspect.*—Rounded.

*Length of lateral branches.*—35.6 cm.

*Diameter of lateral branches.*—0.3 cm at the widest point.

*Internode length on lateral branches.*—5.7 cm.

*Attitude.*—Upright; angle is approximately 30 degrees from vertical.

*Strength.*—Strong.

*Texture and luster.*—Glabrous and moderately glossy.

*Color, juvenile.*—Yellow-green, nearest to RHS 146B; surfaces exposed to sunlight are a darker shade of yellow-green, nearest to RHS 152A.

*Color, mature.*—Yellow-green, nearest to a mixture of RHS 146B and 146C; surfaces exposed to sunlight are greyed-brown, nearest to a mixture of RHS N199A and N199B, and heavily suffused with yellow-green, nearest to RHS 152A.

*Color at internodes.*—Yellow-green, nearest to RHS 144A; surfaces exposed to sunlight are greyed-orange, nearest to in between 166A and 166B.

*Color of bark on main stems.*—Greyed-brown, nearest to a mixture of RHS N199C and N199D.

Foliage:

*Arrangement.*—Opposite.

*Division.*—Simple.

*Quantity.*—Average of 14 leaves per lateral branch.

*Lamina.*—Dimensions — 6.3 cm long and 4.7 cm wide, on average. Shape — Obovate to broad elliptic. Aspect — Flat to very slightly carinate. Apex — Short apiculate to abruptly acute. Base — Rounded to truncate. Margin — Entire; not undulated. Pubescence, texture and luster of adaxial surface — Glabrous, smooth, and glossy. Pubescence, texture and luster of abaxial surface — Glabrous, smooth, and moderately glossy. Color — Juvenile foliage, adaxial surface — Nearest to in between green and yellow-green, RHS 137A and 146A, but slightly darker. Juvenile foliage, abaxial surface — Yellow-green, nearest to in between 146A and 146B. Mature foliage, adaxial surface — Nearest to in between green and greyed-green, RHS 139A and N189A, but darker. Mature foliage, abaxial surface — Yellow-green, nearest to in between RHS 146B and 147B. Venation — Pattern — Pinnate. Venation color, adaxial surface — Yellow-green, nearest to RHS 144A. Venation color, abaxial surface — Yellow-green, nearest to RHS 145B.

*Petiole.*—Length — 1.3 cm. Width — 0.15 cm. Texture — Smooth and glabrous. Luster — Moderately glossy. Strength — Moderately strong. Color, adaxial surface — Yellow-green, nearest to RHS 152A. Color, abaxial surface — Yellow-green, nearest to RHS 145A.

Inflorescence:

*Inflorescence arrangement.*—Axillary raceme bearing 2 to 6 flowers.

*Natural flowering season.*—Long flowering period; spring through autumn in USDA Hardiness Zones 10 through 12.

*Time to flower.*—Approximately 10 weeks from planting a rooted cutting.

*Dimensions.*—13.2 cm long and 10.1 cm in diameter.

*Quantity of flowers per inflorescence.*—4 on average; varying from 3 to 5.

*Quantity of flowers per plant.*—5.

*Quantity of flower buds per plant.*—31.

*Quantity of flowers and flower buds per plant.*—36.

*Peduncle.*—Dimensions — 6.8 cm long and 0.2 cm in diameter. Aspect — Upward and outward; at approximately 30 degrees to the lateral branch axis. Strength — Moderately strong. Texture and luster — Glabrous and moderately glossy. Color — Green, nearest to a mixture of RHS 143A and 143B.

Bud:

*Shape.*—Narrow oblanceolate.

*Dimensions.*—5.3 cm long and 0.9 cm in diameter.

*Pubescence, texture and luster.*—Glabrous, smooth and very slightly glossy.

*Color.*—The distal one-quarter portion of the bud is red, nearest to RHS 39B; the middle portion is yellow-green, nearest to RHS 145C; and, the proximal one-third portion of the bud is yellow-green, nearest to RHS 145A.

Flower:

*Flowering habit.*—Moderately free flowering.

*Shape.*—Funnelform.

*Flower vertical height.*—6.8 cm.

*Flower width.*—6.8 cm.

*Flower depth.*—6.3 cm.

*Aspect.*—Flowers are outward facing.

*Fragrance.*—A faint pleasant fragrance; acidic-sweet.

*Lastingness.*—Approximately 10 days.

*Persistent.*—Self-cleaning.

*Pedicels.*—Dimensions — 1.8 cm long and 0.2 cm in diameter. Aspect — Upward and outward; approximately 30 degrees to the peduncle axis. Strength — Moderately strong. Texture and luster — Glabrous, smooth, and moderately glossy. Color — Yellow-green, nearest to RHS 152B.

*Corolla throat.*—Shape — In between cylindrical and conical. Depth — 3.3 cm. Diameter — 1.3 cm. Texture — Glabrous; smooth. Outer color — Red-purple, nearest to RHS 62D. Inner color — Red-purple, nearest to RHS 62C, and fading to orange-red towards the narrowest portion of the throat, nearest to a mixture of RHS 34A and 34B. Veins are yellow-orange, nearest to RHS 18B.

*Corolla tube.*—Shape — Near cylindrical. Depth — 1.8 cm. Diameter — 0.4 cm, distally, where the tube begins to widen. Texture — Glabrous; smooth. Outer color, when fully opened — Yellow-green, nearest to RHS 145A. No visible venation. Inner color, when fully opened — Yellow-green, nearest to RHS 151D. No visible venation.

*Petals.*—Quantity of Petals — 5. Arrangement — Single whorl; petals imbricate and fused into an elongated tube at the base; two-thirds of the petals are fused. Shape of petal lobes — Spatulate. Dimensions, free portion of petals — 7.9 cm long and 3.3 cm wide. Apex — Unequal short apiculate. Base — Truncate; fused at the base. Margin — Entire; moderately to highly undulated. Aspect — Moderately reflexed. Pubescence, texture and luster of upper surface — Glabrous, velvety and very slightly glossy. Pubescence, texture and luster of lower surface — Glabrous, moderately velvety and slightly glossy. Petal lobe color when opening, upper surface — Red-purple, nearest to RHS N57B, and fading to a lighter shade of red-purple towards the throat, nearest to RHS 62C. Petal lobe color when opening, lower surface — Red-purple, nearest to RHS 62A; central longitudinal band and base of the petals towards the floral throat are red-purple, RHS 69D. Petal lobe color when fully opened, upper surface — Red-purple, nearest to RHS 62A, and becoming darker towards the margins, nearest to RHS 61D; lighter towards the throat, nearest to RHS 62C. No visible venation. Color do not fade with age. Petal lobe color when fully opened, lower surface — Red-purple, nearest to a mixture of RHS 69B and 69C, and fading darker towards the margins, nearest to RHS 62B. No visible venation. Colors do not fade with age.

*Calyx.*—Shape — Rotate; single whorl of sepals. Dimensions — 0.6 cm in diameter and 0.5 cm tall. Sepals — Calyx dimensions — 0.7 cm in diameter and 0.2 cm tall. Arrangement — Sepals are free, rotate. Quantity — 5. Shape — Narrow triangular to lanceolate. Sepal dimensions — 0.7 cm long and 0.2 cm wide at the base. Apex — Narrow acuminate. Base — Cuneate. Margin — Entire; not undulated. Pubescence, texture and luster, upper surface — Smooth; glabrous; slightly glossy. Pubescence, texture and luster, lower surface — Smooth; glabrous; very slightly glossy. Color when opening, upper surface — Yellow-green, nearest to RHS 145A; apex is suffused with greyed-red, nearest to RHS 179B. Color when opening, lower surface — Yellow-green, nearest to RHS 145A; apex is suffused with greyed-red, nearest to RHS 179B. Color when fully opened, upper surface — Yellow-green, nearest to RHS 145A; moderately to heavily suffused with greyed-red, RHS 181B, at the apex. Color when fully opened, lower surface — Yellow-green, nearest to RHS 145A; moderately to heavily suffused with greyed-red, RHS 181B, at the apex.

Reproductive organs:

*Androecium.*—Stamen quantity — 5. Attachment — Adnate. Filament length — 0.3 cm. Filament color — Yellow-green, nearest to RHS 151D. Anther attachment — Basifixed. Anther shape — Narrow sagitate. Anther length — 1.0 cm. Anther width — 0.125 cm. Anther color — Greyed-yellow, nearest to RHS 162C. Anther aspect — The five anthers are touching at their apices, thus forming a cone of anthers. Pollen, presence — Scarce. Pollen color — White, RHS 155A.

*Gynoecium.*—Pistil quantity — One. Pistil length — 2.3 cm. Style length — 2.1 cm. Style color — Yellow-green, nearest to RHS 150D. Stigma shape — Club-shaped. Stigma length — 0.2 cm. Stigma diameter — 0.2 cm. Stigma color — Yellow-green, nearest to RHS 150B. Ovary color — Yellow-green, nearest to RHS 144C.

Seed and fruit: None observed.

COMPARISONS WITH THE PARENT PLANTS

Plants of the new cultivar 'PATMANROS3' differ from the seed parent, *Mandevilla* 'Velvet' (not patented) by the characteristics described in Table 1.

TABLE 1

| Characteristic | 'PATMANROS3' | 'Velvet' |
|---|---|---|
| General coloration of the flowers when fully opened. | Very light red-purple and becoming progressively darker towards the margins. | Medium to dark red-purple. |

COMPARISON WITH THE MOST SIMILAR *MANDEVILLA* CULTIVAR KNOWN TO THE INVENTOR

Plants of the new cultivar 'PATMANROS3' differ from the commercial variety, *Mandevilla* 'PATMANCR' (U.S. Plant Pat. No. 29,797), in the following characteristics described in Table 2 below.

TABLE 2

| Characteristic | 'PATMANROS3' | 'PATMANCR' |
|---|---|---|
| Growth habit. | More free branching and more densely foliaged than 'PATMANCR' | Less branching and less densely foliaged than 'PATMANROS3'. |
| Flower size. | Smaller than 'PATMANCR'. | Larger than 'PATMANROS3'. |
| General coloration of the flowers when fully opened. | Very light red-purple and becoming progressively darker towards the margins. | Light red-purple. |

That which is claimed is:

1. A new and distinct variety of *Mandevilla* plant named 'PATMANROS3', substantially as described and illustrated herein.

* * * * *